(12) United States Patent
Bruce

(10) Patent No.: US 6,541,987 B1
(45) Date of Patent: Apr. 1, 2003

(54) LASER-EXCITED DETECTION OF DEFECTIVE SEMICONDUCTOR DEVICE

(75) Inventor: Michael R. Bruce, Austin, TX (US)

(73) Assignee: Advanced Micro Devices, Inc., Sunnyvale, CA (US)

( * ) Notice: Subject to any disclaimer, the term of this patent is extended or adjusted under 35 U.S.C. 154(b) by 0 days.

(21) Appl. No.: 09/385,775

(22) Filed: Aug. 30, 1999

(51) Int. Cl.[7] .............................................. G01R 31/302
(52) U.S. Cl. ...................................... 324/752; 324/765
(58) Field of Search ................................. 324/750, 751, 324/752, 765, 767, 71.6, 719; 438/14–18; 257/40–48; 250/492.1, 459.1; 356/318, 237.1, 417

(56) References Cited

U.S. PATENT DOCUMENTS 5,334,540 A * 8/1994 Ishii ........................... 324/765
5,541,416 A * 7/1996 Washizula ................ 250/459.1
6,081,127 A * 6/2000 Wagner et al. ............. 324/765

OTHER PUBLICATIONS

Sidney Perkowitz, "Optical Characterization of Semiconductors: Infrared, Raman, and Photoluminescence Spectroscopy," Academic Press Limited, 1993, pp. 1–4, 50–57, 61–65, 74–83, 105–109, (month unavailable).

* cited by examiner

Primary Examiner—Vinh P. Nguyen

(57) ABSTRACT

Useful in connection with IC testing at a post-manufacture stage, an example embodiment is directed to use of photoluminescence PL spectroscopy for detecting contaminants in circuit materials. According to one example embodiment, a system includes a test fixture arranged to secure a die and includes a laser-scanning microscope. This system is arranged to direct a laser beam at a target material in the die and receives a secondary PL component remitted from the target circuit material. A contaminant in the target material is indicated by the reception of the secondary PL component.

23 Claims, 2 Drawing Sheets

LASER-EXCITED DETECTION OF DEFECTIVE SEMICONDUCTOR DEVICE

FIELD OF THE INVENTION

The invention relates to defect analysis in semiconductor device assemblies, and more particularly to techniques for accurately analyzing defects within semiconductor devices using laser scanning microscopes.

BACKGROUND OF THE INVENTION

The semiconductor industry has seen tremendous advances in technology in recent years that have permitted dramatic increases in circuit density and complexity, and equally dramatic decreases in power consumption and package sizes. Present semiconductor technology now permits single-chip microprocessors with many millions of transistors, operating at speeds of tens (or even hundreds) of MIPS (millions of instructions per second) to be packaged in relatively small, air-cooled semiconductor device packages. A by-product of such high-density and high functionality in semiconductor devices has been an increased demand in the numbers of external electrical connections present on the exterior of the die and on the exterior of the semiconductor packages which receive the die, in order to connect the packaged device to external systems, such as a printed circuit board.

Typically, dies contain a bonding pad which makes the electrical connection to the semiconductor package. To shorten the electrical path to the pad, the bonding pads were moved to the side of the die nearest the transistors and other circuit devices formed in the die. Connection to the package is made when the chip is flipped over and soldered. As a result, the dies are commonly called flip chips in the industry. Each bump on a pad connects to a corresponding package inner lead. The resulting packages are lower profile and have lower electrical resistance and a shortened electrical path. The plurality of ball-shaped conductive bump contacts (usually solder, or other similar conductive material) are typically disposed in a rectangular array. These packages are occasionally referred to as "Ball Grid Array" (BGA) or "Area Grid Array" packages.

A typical BGA package is characterized by a large number of solder balls disposed in an array on a surface of the package. It is not uncommon to have hundreds of solder balls in an array. The BGA package is assembled to a matching array of conductive pads. The pads are connected to other devices within a substrate or circuitry on a circuit board. Heat is applied to reflow the solder balls (bumps) on the package, thereby wetting the pads on the substrates and, once cooled, forming electrical connections between the package and the semiconductor device contained in the package and the substrate.

The introduction of flip chips and Ball Grid Array (BGA) packages to the semiconductor industry has brought several new manufacturing and assembly challenges. One of the more significant problems is finding an efficient, cost-effective technique for analyzing the flip chips and BGA packages for defects.

One method for detecting defects in a circuit includes the use of Light Induced Voltage Alteration (LIVA). LIVA requires that a beam of electromagnetic radiation, typically a laser, be directed at a circuit. The electromagnetic radiation causes a change in voltage within the circuit. This change in voltage is measured and used as an indication of a defect, such as a short.

Another method for detecting defects in a circuit includes the use of a photoemission microscope to view a circuit that is powered. Defects within the powered circuit give off a photoemission, which is then recorded with the photoemission microscope. The difficulty in using this method is that in some cases the location of the defect must be known prior to the use of a photoemission microscope.

As more capability is being designed into electronic devices, such as memory chips and microprocessor chips, the number of input/output elements, pads, and connections between other devices are being vastly increased. Therefore, a controlled and efficient process for analyzing defects is becoming even more important.

SUMMARY OF THE INVENTION

The method described herein involves the use of a laser to scan the back side of a semiconductor, such that it excites all of the nodes within the semiconductor. The laser excites the nodes within the semiconductor by exposing the nodes to laser light, which causes the nodes to absorb a photon. When there is a defect, such as a short in the circuit, those nodes associated with a defect give off a photoemission of a different wavelength than the photoemission given off by non-defective semiconductors. The photoemission is then recorded with a photoemission microscope. The ability to scan an entire surface and discover a defect, rather than having to know beforehand where the defect is located, is an improvement upon the efficiency of the defect analysis of semiconductors.

In one embodiment of the invention, a method for analyzing a circuit in a semiconductor device is achieved by directing a laser beam having a known wavelength at a target material in the semiconductor device, receiving a secondary photoluminescent (PL) component remitted by the target material, and, therefrom, detecting a contaminant in the target material.

In another example embodiment, a method for analyzing an electronic circuit is formed upon a front side surface of a semiconductor device having opposing front side and back side regions. The method comprises scanning the back side surface with a laser beam having a known wavelength and detecting a photoemission response from the electronic circuit. The wavelength of the response from defective semiconductors is different from the wavelength of the response from non-defective semiconductors.

In yet another example embodiment, a system for analyzing an electronic circuit comprises a test fixture that is arranged to secure a die which includes the electronic circuit and an LSM that is arranged to direct a laser beam at a target material in the die and receive a secondary photoluminscent (PL) component which may be remitted from the target material.

BRIEF DESCRIPTION OF THE DRAWINGS

The invention may be more completely understood in consideration of the following detailed description of various embodiments of the invention in connection with the accompanying drawings, in which.

Figure 1:
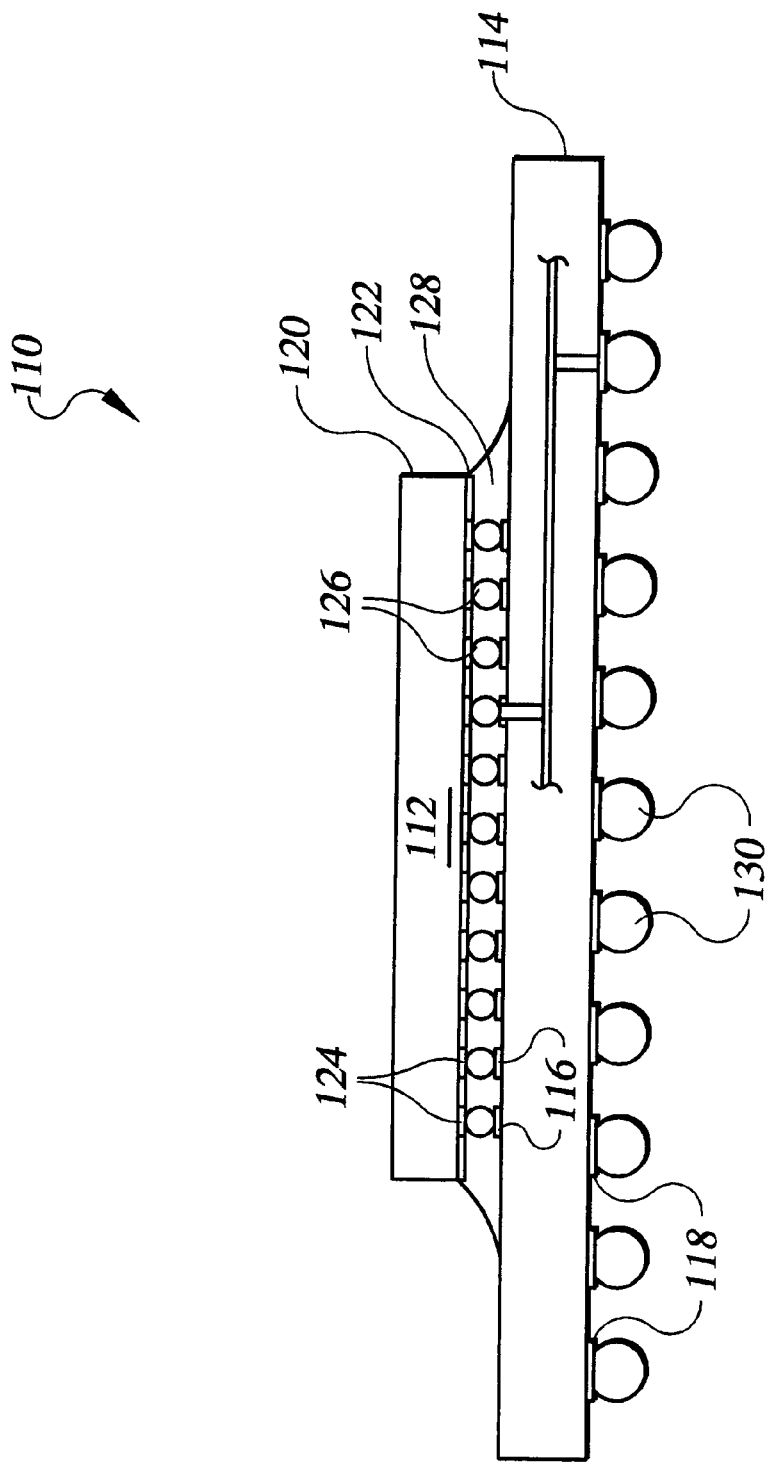
FIG. 1 shows a conventional flip-chip semiconductor device.

While the invention is amenable to various modifications and alternate forms, specifics thereof have been shown by way of example in the drawings and will be described in detail. It should be understood, however, that the intention is not to limit the invention to the particular embodiments described. On the contrary, the intention is to cover all modifications, equivalents, and alternatives falling within the spirit and scope of the invention as defined by the appended claims.

DETAILED DESCRIPTION

The present invention is advantageous in connection with failure analysis of a variety of semiconductor devices, including complex, high-density integrated circuits. Due to a shortage of space for I/O (input/output) parts, such integrated circuits are sometimes packaged as "flip-chips."

In "flip-chip" packaging, bonding pads and metal (solder) bumps are used for I/O. The bonding pads need not be on the periphery of the die and hence are moved to the site nearest the transistors and other circuit devices formed in the die. As a result, the electrical path to the pad is shorter. Electrical connection to the package is made when the die is flipped over the package with corresponding bonding pads. Each bump connects to a corresponding package inner lead. The resulting packages have a lower profile and have lower electrical resistance and a shortened electrical path. The output terminals of the package may be ball-shaped conductive-bump contacts (usually solder, or other similar conductive material) are typically disposed in a rectangular array. These packages are occasionally referred to as "Ball Grid Array" (BGA) packages. Alternatively, the output terminals of the package may be pins; such a package is commonly known as a Pin Grid Array (PGA) package.

A package of this type is an example target application of embodiments of the present invention, and a flip-chip packaged die is used as an example application for embodiments addressed below.

FIG. 1 shows a conventional flip chip device illustrating both a target and end-product of a reconstruction approach, according to an example application of the present invention. Such a circuit modification process is applicable to a conventional flip-chip type die such as the die 110 of FIG. 1 shown from a side view along with an attached package substrate 114. Flip-chip die 112 has a back side 120 and a circuit side in a portion of the die known as the epitaxial layer 122. The epitaxial layer 122 includes a number of circuit devices and has a thickness in the range of one to fifteen microns. Bulk silicon fills the back side 120 and is referred to as the bulk silicon layer. A plurality of solder bumps 126 are made on the circuit side at pads 124. The solder bumps 126 are the inputs and outputs to the circuitry associated with the flip-chip type die 112. The flip-chip type die 112 is attached to the package substrate 114 via the solder bumps on the die 112. The package substrate 114 includes pads 116 that are arranged to correspond to the pattern of solder bumps 126 on the die 112. The region between the die 112 and package substrate 114 is filled with an under-fill material 128 that encapsulates the solder bump connections and provides additional mechanical benefits. The pads 116 are coupled via circuitry to pads 118 on the package substrate, and solder bumps 130 are formed on the pads 118. The solder bumps 130 are the inputs and outputs to the circuitry associated with the package substrate 114.

For a flip-chip type die such as die 112 of FIG. 1, failure analysis is usually accomplished using a global and/or local thinning process. Example implementations for such thinning include: mechanically polishing, laser-microchemically etching, and ion bombardment, such as using a focused ion beam (FIB) system. For the above-mentioned circuit modification activity, the die 112 can be globally or locally thinned relatively close to the epitaxial layer 122, at which point the final access path for reconstruction begins.

Figure 2:
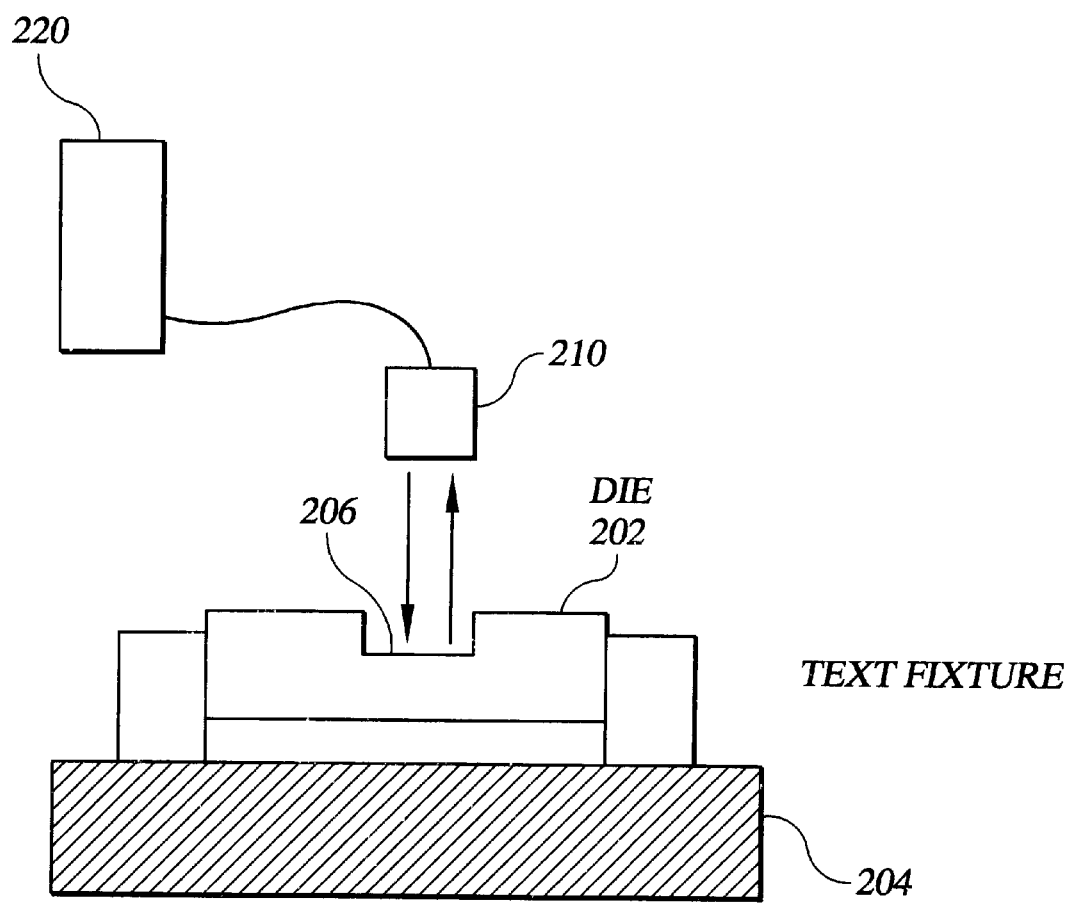
FIG. 2 shows a system for detecting defects in semiconductor devices, according to the present invention.

FIG. 2 illustrates a system 200 for analyzing an integrated circuit die 202. In a first embodiment, the die 202 can be of the type illustrated in FIG. 1, and in a second embodiment, the die 202 is packaged in a normally-oriented package. In another embodiment, circuitry for analysis is prepared for placement in test fixture 204 and processing by the system 200.

For a flip-chip package, processing includes thinning of the substrate back side, for example, by first chemically-mechanically polishing (CMP) the entire back side to within about 100 microns of the active circuitry region. Such thinning is referred to as "global thinning" and may also be accomplished by other techniques such as ion bombardment, laser etching and other chemical processes.

Preferably, a working area 206 is created in the form of a trench over the target area for analysis. This working area 206 can be realized by "locally thinning" the substrate using a process that is slower, easier to stop, and more refined than most CMP processes and various global thinning techniques.

For example, micro laser etching and focused-ion beam etching processes are more suitable for forming such a working area 206. In one example application suitable for a flip-chip die, the working area is a 10 micron by 15 micron square having a floor that is a few to several microns over an n-well target material for analysis.

With the die 202 secured by the text fixture 204, a laser source and laser detector arrangement 210 is used optically to characterize the quality (purity versus impurity) of the target material. One useful device that implements this source/detection arrangement is a laser-scanning microscope (LSM) such as models 321 and 321IR available from Carl Zeiss, Inc. The 321 device operates in the visible light spectrum, whereas the 321IR operates in the near infrared (nIR) light spectrum.

Where the target material of the die 202 does not contain any significant (i.e., noticeable) impurities, the arrangement 210 detects reflected light having only the wavelength of the source laser beam. For impure target materials, the target material reflects the laser corresponding to the wavelength of the source laser beam, and also a second PL component that corresponds to a shift in the spectrum from the wavelength of the source laser. The system 200 can include a computer (220) for comparing magnitudes of second PL components generated by suspect devices with that of non-defective devices having substantially pure target material(s); where this magnitude of a suspect device does exceed that of the non-defective device by more than a tolerance differential, the suspect device is considered non-defective.

In a particular example application consistent with the above-described working area for the flip-chip die 202 of FIG. 2, the arrangement 210 is implemented using an Ar+ laser adapted to source a 250 mw, 514 nm wavelength beam at a target silicon material that has been contaminated (intentionally or unintentionally) with aluminum at a concentration of about $3.0 \times 10^{14}$ $cm^{-3}$. The LSM used in the arrangement 210 of FIG. 2 typically evidences the above-discussed first and second PL components, with the second PL component having a noticeable count of photons per unit energy, but shifted along the spectrum on the order of 10% to 15%. For a first component detected at 1150 meV, the light remitted by the aluminum concentrated material has a wavelength of between 1090 nm and 1100 nm.

Other impurities are similarly detected in silicon and other materials used in such semiconductor devices. For example, fingerprint contaminants such as sodium are also readily detectable using this PL-LSM approach. The skilled artisan will also appreciate that such materials include but are not limited to: silicon, silicon dioxide as used in trench isolation structures, and doped concentrations of silicon such as used in source/drain and polysilicon gate regions. The possible contaminants for each such material are too numerous to mention each, but some of the more common contaminants include: carbon, potassium and copper. For further details on the theory of PL and various case studies on the same, reference may be made to "Optical Characterization of Semiconductors: Infrared, Ramon and Photoluminescence Spectroscopy," Sidney Perkowitz, Academic Press, 1993.

Accordingly, various embodiments of the present invention provide approaches for determining whether defects, in the form of material impurities, are present in semiconductor materials for immediate applicability to device analysis, debugging and general improvements to the manufacturing processes of integrated circuits.

What is claimed is:

1. A method for analyzing an electronic circuit in a semiconductor device comprising:
   directing a laser beam having a known wavelength at a target material in the semiconductor device;
   receiving a secondary photoluminescent (PL) component remitted by the target material; and
   detecting a contaminant in the target material as a function of the wavelength of the secondary PL component.

2. A method according to claim 1, further including using an LSM (laser scanning microscopy) device to direct the laser beam.

3. A method, according to claim 2, wherein the known wavelength is in the visible light spectrum.

4. A method, according to claim 3, further including exposing circuitry in the target material before directing a laser beam at the target material.

5. A method, according to claim 4, wherein the target material is in a normally-oriented (non-flip-chip) package.

6. A method, according to claim 2, wherein the known wavelength is in the near IR light spectrum.

7. A method, according to claim 2, wherein directing at the target material includes directing at an intervening region of silicon directly over the target material.

8. A method, according to claim 7, wherein the target material is in the epitaxial region of a flip-chip type package.

9. A method, according to claim 1, wherein detecting includes comparing the secondary PL component to a threshold.

10. A method, according to claim 1, wherein detecting a contaminant as a function of the wavelength of the secondary PL component includes detecting that the wavelength is different than a wavelength of non-defective target material.

11. A method, according to claim 1, wherein detecting a contaminant as a function of the wavelength of the secondary PL component includes detecting that the wavelength is different than the known wavelength of the laser.

12. A method, according to claim 1, wherein directing a laser beam at a target material includes scanning the laser beam across the semiconductor device, wherein receiving a secondary PL component remitted by the target material includes receiving a secondary PL component from a plurality of target material in the semiconductor device and wherein detecting a contaminant in the target material includes detecting that the secondary PL component from a portion of target material in the device is different from the secondary PL component from a different portion of target material in the device.

13. A method for analyzing an electronic circuit formed upon a front side surface of a semiconductor device having opposing front side and back side regions, the method comprising:
   scanning the back side with a laser beam having a known wavelength; and
   detecting a photoemission response from the electronic circuit, the response being indicative of a defect when the wavelength of the response is different from the wavelength of the response from non-defective semiconductors.

14. A method, according to claim 13, wherein detecting a photoemission response includes comparing a secondary PL component with a prestored reference.

15. A system for analyzing an electronic circuit, comprising:
   a test fixture arranged to secure a die including the electronic circuit;
   an LSM arranged to direct a laser beam at a target material in the die and to receive a secondary PL component remitted from the target material, wherein a contaminant in the target material is indicated by the reception of the secondary PL component having a wavelength different from that of non-defective target material.

16. A system, according to claim 15, further including means for comparing an attribute of the secondary PL component to a prestored threshold.

17. A system, according to claim 16, wherein the LSM is adapted to direct light in the visible spectrum.

18. A system, according to claim 16, wherein the LSM is adapted to direct light in the near IR spectrum.

19. A system, according to claim 15, wherein the LSM is adapted to direct light in the visible spectrum.

20. A system, according to claim 15, wherein the LSM is adapted to direct light in the near IR spectrum.

21. A system for analyzing an electronic circuit, comprising:
   a test fixture arranged to secure a die including the electronic circuit;
   a means for directing a laser beam at a target material in the die and to receive a secondary PL component remitted from the target material, wherein a contaminant in the target material is indicated by the reception of the secondary PL component having a wavelength different from that of non-defective target material.

22. A system according to claim 21, wherein the test fixture is arranged to secure a flip chip die.

23. A system according to claim 21, wherein the test fixture is arranged to secure a normally-oriented die.

* * * * *